United States Patent
Alur

(10) Patent No.: US 8,461,210 B2
(45) Date of Patent: Jun. 11, 2013

(54) FAST RELEASE PARACETAMOL TABLETS

(75) Inventor: Hemant H. Alur, Parsippany, NJ (US)

(73) Assignee: GlaxoSmithKline, LLC, Philadelphia, PA (US)

( * ) Notice: Subject to any disclaimer, the term of this patent is extended or adjusted under 35 U.S.C. 154(b) by 431 days.

(21) Appl. No.: 12/295,941

(22) PCT Filed: Apr. 3, 2007

(86) PCT No.: PCT/US2007/065829
§ 371 (c)(1),
(2), (4) Date: Oct. 3, 2008

(87) PCT Pub. No.: WO2007/118063
PCT Pub. Date: Oct. 18, 2007

(65) Prior Publication Data
US 2009/0170955 A1      Jul. 2, 2009

(30) Foreign Application Priority Data

Apr. 7, 2006   (GB) .................................. 0607085.8

(51) Int. Cl.
*A61K 31/16*   (2006.01)

(52) U.S. Cl.
USPC ...................................................... 514/629

(58) Field of Classification Search
USPC ...................................................... 514/629
See application file for complete search history.

(56) References Cited

U.S. PATENT DOCUMENTS

| 6,316,025 | B1 | 11/2001 | Grattan |
| 2004/0170681 | A1 | 9/2004 | Grattan |
| 2005/0276847 | A1 | 12/2005 | Roberts et al. |
| 2007/0141144 | A1 | 6/2007 | Roberts et al. |
| 2007/0298096 | A1 | 12/2007 | Liu et al. |

FOREIGN PATENT DOCUMENTS

| EP | 0 396 972 | | 11/1990 |
| EP | 0 418 564 | | 3/1991 |
| GB | 2 103 087 | | 2/1983 |
| WO | WO 98/38983 | * | 9/1998 |
| WO | 02/100391 | | 12/2002 |
| WO | 2005/115344 | | 12/2005 |
| WO | 2005/115345 | | 12/2005 |
| WO | 2006/049978 | | 5/2006 |
| WO | 2007/059591 | | 5/2007 |

OTHER PUBLICATIONS

Swarbrick, Encyclopedia of Pharmaceutical Technology, vol. 20, pp. 285 and 286 (2000).*
Swarbrick (Encyclopedia of Pharmaceutical Technology, vol. 20).*
Swarbrick, James et al., Encyclopedia of Pharmaceutical Technology, vol. 20, 2000. (Previously cited and copy provided on Mar. 4, 2011).*
Grattan, et al., European J. of Pharmaceutics and BioPharmaceutics, vol. 49(3) pp. 225-229 (2000).
Xiuzhi, et al., Chinese J. of Pharmaceutics, vol. 23(9) pp. 400-402 (1992).
Rostami, et al., Drug Development and Industrial Pharmacy, vol. 28(5) pp. 523-531 (2002).
Rostami, et al., Drug Development and Industrial Pharmacy, vol. 28(5) pp. 533-543 (2002).
Shijue, et al., Yiyao Gongye, vol. 2 pp. 21-25 (1984).

* cited by examiner

*Primary Examiner* — Frederick Krass
*Assistant Examiner* — Adam C Milligan
(74) *Attorney, Agent, or Firm* — Nora L. Stein; Theodore R. Furman

(57) ABSTRACT

A pharmaceutical composition such as a swallow tablet or capsule formulation is described comprising paracetamol, calcium carbonate, at least one binding agent and at least one disintegrating agent in the form of a granulate, optionally combined with one or more pharmaceutically acceptable extragranular components.

31 Claims, No Drawings

FAST RELEASE PARACETAMOL TABLETS

This application is a 371 of International Application No. PCT/US07/65829, filed 3 Apr. 2007.

The present invention relates to pharmaceutical compositions containing N-acetyl-p-aminophenol, known by the generic names paracetamol, acetaminophen and APAP (hereinafter referred to as paracetamol). In particular, the invention relates to an immediate release, fast-acting paracetamol formulation containing calcium carbonate.

Paracetamol is a commonly used analgesic and antipyretic drug that has been available in many countries for more than 40 years. A wealth of experience clearly establishes it as the standard antipyretic and analgesic for mild to moderate pain states. Paracetamol is available in many countries for non-prescription over-the-counter sale in conventional liquid, suppository, capsule, tablet and caplet dosage forms. Following ingestion of paracetamol in solid form, e.g. as a tablet or capsule, rate of drug absorption, and onset of pharmacological activity, may vary from patient to patient. For example it has been shown that absorption of paracetamol in tablet form is greatly affected by food and that minimum therapeutic concentrations of paracetamol are not always reached, which could have implications for pain relief in some patients (Stillings M. et al, Current Medical Research and Opinion 16(2): 115-124, 2000).

Many attempts have been made to improve the rate of onset of activity, for example, by the provision of soluble tablets, such as those available commercially under the Panadol® brand. Such tablets have been shown to have a faster rate of absorption (Rygnestad T et al., Eur J Clin Pharmacol 56: 141-143, 2000) and a faster onset of analgesic action compared to conventional paracetamol tablets (Moeller P L. et al., J Clin Pharmacol. 40: 370-378, 2000). However soluble tablets are not always convenient as they have to be dissolved in water prior to administration and moreover paracetamol-containing solutions are unpalatable to some patients. Furthermore many soluble tablets also contain high levels of sodium bicarbonate, and so are not appropriate for use in all patients, for example in patients that are on a restricted sodium diet.

An alternative dosage form that comprises a rapidly absorbed form of paracetamol, is available commercially in the form a swallow tablet under the Panadol brand, namely Panadol Actifast®. However this swallow tablet also comprises a large amount of sodium bicarbonate. Moreover this tablet is of a large size and some patients experience difficulties in swallowing the tablet.

Consequently there remains a need for improved formulations; ideally, such formulations would offer one or more of the following advantages:
 i.) a fast dissolution profile resulting in improved absorption kinetics, irrespective of the dietary state of the patient;
 ii.) demonstrate less variable absorption (both between subjects and within subjects);
 iii.) be suitable for long-term use e.g. as may be required by users that suffer from chronic illness and who may require pain relief on a daily basis;
 iv.) be suitable for use by users on a restricted sodium or potassium diet;
 v.) afford the convenience of a swallow tablet, including being of a small tablet size and easy to swallow;
 vi.) provide a product of acceptable long term storage stability; and
 vii.) be economical to manufacture, and be sufficiently robust so as to be capable of withstanding packaging, shipping and handling operations.

It is an object of the present invention to provide such an improved formulation.

One aspect of the invention provides a fast release, stable paracetamol composition comprising paracetamol, calcium carbonate, at least one binding agent and at least one disintegrating agent in the form of a granulate.

A fast release paracetamol composition according to the invention disintegrates and dissolves rapidly in the stomach so as to facilitate fast absorption of paracetamol into the circulatory system. For purposes herein, "fast release" means wherein at least 60% e.g. at least 70%, e.g. at least 80%, e.g. at least 90%, of the paracetamol has dissolved from the composition at 180 seconds, as determined by the dissolution testing method described herein. This dissolution testing method utilizes the same conditions as used in the method disclosed in WO 02/100391, namely a USP paddle apparatus rotating at 30 rpm, employing 900 ml of 0.05M HCl at 37° C. as the dissolution medium, although percentage of paracetamol dissolved is determined at 180 seconds, rather than at fifteen minutes as determined in the method described in WO 02/100391, which is incorporated herein by reference. A measurement taken at 180 seconds, rather than at fifteen minutes, has been found to be more discriminating and a better predictor of in vivo dissolution rate for compositions according to the invention. Paracetamol release rate has been determined for a number of commercially available paracetamol products and found to range from about 12% to about 32%, as determined at 180 seconds by the dissolution testing method described herein. Advantageously a composition according to the invention, comprising a release rate of 60% or more, represents a significant increase in the release rate, and hence absorption rate of paracetamol, compared to the commercially available paracetamol products tested.

For purposes herein "stable" means wherein the composition, when suitably packaged, is stable on storage under ambient conditions of temperature and humidity for a period of time, suitably for at least a number of months. In one aspect, a pharmaceutical composition of the invention is sufficiently stable so as to provide a commercially viable product having a shelf life of at least eighteen months, typically two to three years, including a dissolution rate that does not adversely deteriorate on storage. Stability and shelf-life determination of pharmaceutical products may be determined by carrying out "real time" storage stability trials under ambient conditions, or alternatively may be predicted from short-term accelerated stability trials. Accelerated stability trials are common practice in the pharmaceutical industry and are an important and recognized indicator of commercial viability of any given pharmaceutical formulation. An accelerated stability test used herein involves storing the pharmaceutical composition, in an open Petri dish under stressed conditions of temperature, e.g. 40° C.±2° C., and relative humidity (RH), e.g. 75% RH±5% RH, for a relatively short period of time e.g. five days or more, suitably ten days, and then applying the dissolution testing method to determine paracetamol release rate i.e. percentage paracetamol dissolved at 180 seconds. A composition according to the invention is considered sufficiently stable so as warrant a shelf life of at least eighteen months when the paracetamol release rate from the composition, as determined by the accelerated stability test used herein, remains at least 60% e.g. at least 70% e.g. at least 80% released at 180 seconds.

Accordingly one aspect of the invention provides a pharmaceutical composition comprising paracetamol, calcium carbonate, at least one binding agent, and at least one disintegrating agent, as intragranular components in the form of a granulate, and wherein at least 60% of the paracetamol is released from the composition at 180 seconds as determined by a dissolution method that utilizes a USP paddle apparatus rotating at 30 rpm, employing 900 ml of 0.05M HCl, following storage of the composition for ten days in an open Petri dish at 40° C.±2° C., and 75% RH±5% Relative Humidity (RH).

The granulate may optionally be combined with one or more suitable extragranular components as will be defined hereinafter. In unit dosage form, a pharmaceutical composition of the invention is in the form of a swallow formulation that is intended to be swallowed whole and is not designed to be dispersed in the mouth or dissolved or suspended in water prior to administration. In one embodiment the composition is in the form of a tablet, i.e. a swallow tablet. The term "tablet" as used herein includes tablets of any shape, and includes caplets, which are tablets having a capsule shape. Suitably a tablet according to the invention is compressed to a hardness of 5-16 kP. Typically, round tablets are compressed to a hardness of 5-10 kP. Typically, caplets are compressed to a hardness of 10-16 kP.

A tablet according to the invention may be coated or uncoated and may be formulated as a homogenous unit, or as a multilayer tablet e.g. a bilayer tablet. A bilayer tablet may have identical, similar or different compositions in each layer of the tablet.

Alternative unit dosage presentations are also envisaged within the scope of the invention. For example a composition according to the invention may be in the form of a capsule, or a powder suitably packaged into a pack such as a stick pack sachet. Suitably the dissolution testing method described herein is carried out on a pharmaceutical composition according to the invention when the composition is in a unit dosage form such as a swallow tablet, a powder preparation or a capsule. It will be understood that when the composition is in the form of a capsule, a sinking aid, such as a "sinker" may be used to prevent the capsule from floating to the top of the dissolution medium. When a composition according to the invention is in the form of "bulk" material prior to being adapted into a unit dosage form, a unit dosage amount of the material may be sampled and tested according to the dissolution testing method described herein.

One aspect of the invention is a granulate i.e. material that has been adapted and preprocessed by suitable means such as slugging, aqueous or non-aqueous wet granulation, fluidized bed granulation, spray drying or roller compaction to form granules. For purposes herein, a component of the granulate is referred to as "intragranular" or an "intragranular component", whereas a component that is admixed with the granulate is referred to as "extragranular" or an "extragranular component". The granulate comprises paracetamol, calcium carbonate, a binding agent and a disintegrating agent and optionally one or more other pharmaceutically acceptable intragranular components. The intragranular components may comprise one or more additional ingredients including but not limited to a processing aid, diluent or filler, colourant, dye, sweetening agent or a mixture thereof.

The granulate so formed provides an intimate admixture of a combination of ingredients and may then be mixed with one or more pharmaceutically acceptable extragranular components of the composition i.e. with any pharmaceutically acceptable ingredient e.g. a diluent, flavor, sweetening agent, glidant, lubricant, anti-adherent, anti-static agent, anti-oxidant, dessicant; or a pharmaceutically active agent; to form a master blend. It is recognized that the same ingredient may be present both as an intragranular and as an extragranular component. The master blend may be compressed into tablets or filled into capsules.

In one embodiment, the granulate is formed by a wet granulation process wherein paracetamol is mixed with other intragranular components including calcium carbonate, a binding agent and a disintegrating agent in a suitable granulator to form a powder blend. Water or a suitable solvent or solvent mixture is added and mixed thoroughly with the powder blend. This process allows the powder blend to become wet and to agglomerate to form granules. In an alternative embodiment, the binding agent or a second binding agent may be dissolved or dispersed in the water or suitable solvent. The wet granules are then dried in a conventional tray drier and then generally milled and screened to obtain granules with a desired particle size distribution.

In another embodiment, the granulate is formed by a fluidized bed granulation process in which the paracetamol, calcium carbonate, binding agent and disintegrating agent and any other desired intragranular components are fluidized in a fluid bed drier and then sprayed with water or suitable solvent. The wet granules so formed are dried and are then generally milled and screened to obtain granules with a desired particle size distribution.

In another embodiment spray granulation is used as a method to granulate powders to obtain spherical free flowing granules. In a spray granulation operation, the paracetamol, calcium carbonate, binding agent, disintegrating agent and other desired intragranular components are suspended in water or suitable solvent. This suspension is sprayed using an atomizer into a spray drier. The droplets so generated by the atomizer are dried to form granules, which are then generally milled and screened to obtain granules with a desired particle size distribution.

In yet another embodiment, roller compaction may be used as a method for manufacture of the granulate, where a dry blend of paracetamol, calcium carbonate, binding agent and disintegrating agent and any other desired intragranular components are forced through a pair of rollers held under high pressure, thereby compacting the powder compacts to form wafer like sheets, which are then generally milled and screened to obtain granules with a desired particle size distribution. Small amounts of water can be sprayed on to the powder blend prior to feeding in to the rollers to enhance the binding properties of the ingredients in this process. The granules so obtained by any of the granulation processes described can be further processed to obtain tablets.

Another aspect of the invention provides a process for the preparation of a pharmaceutical composition. This process comprises preparing a granulate as described above, and optionally admixing the granulate with any other desired extragranular component to form a master blend. The granulate or the master blend may be filled into capsules. Alternatively the master blend may be compressed into tablets.

A pharmaceutical composition according to the invention comprises intragranular paracetamol. Advantageously the amount of paracetamol present intragranularly is relatively high compared to the amount of other components present in the composition, and typically comprises at least 60.0% by weight of the composition. For example in one embodiment the amount of paracetamol present intragranularly is from about 70.0% to about 90.0% by weight of the composition, or from about 60.0% to about 80.0% by weight of the composition in an alternative embodiment. Use of relatively small amounts of other components e.g. excipients, allows comparatively larger amounts of paracetamol to be used without resulting in the production of larger dosage forms as compared to other dosage forms containing the same amount of paracetamol.

When in a unit dosage form, a composition according to the invention comprises a therapeutically effective amount of paracetamol, by which is meant an amount of paracetamol sufficient to achieve a therapeutic benefit. Suitably such an amount is in the range 250 mg to 1000 mg per unit dosage form (e.g. per tablet) and typically is either 325 mg or 500 mg.

Whilst paracetamol is present as an intragranular component, it is recognized that a limited amount of paracetamol e.g. up to about an additional 20.0% by weight of the intragranular paracetamol content of the composition, may also be present extragranularly. In one embodiment a composition according to the invention comprises, as an extragranular component, paracetamol in an amount ranging from about 0.1% to about 10.0% by weight of the intragranular paracetamol amount therein.

A pharmaceutical composition according to the invention comprises paracetamol and calcium carbonate in addition to other components. Paracetamol compositions containing calcium carbonate have previously been described in the art.

According to United Kingdom patent publication GB 2 103 087 (Bristol-Myers), the rate of absorption of paracetamol into the bloodstream, as measured by the $t_{max}$, can be increased if the paracetamol is co-administered with a dose of an antacid that falls in the range of about 60 mg to about 1200 mg with a preferred range being from about 400 mg to about 1000 mg and the optimum range being from about 450 mg to about 880 mg. GB 2 103 087 reports that an increase in the absorption rate, in the range of 7 to 31%, as measured by the $t_{max}$ value, accompanied the administration of compositions of the invention (therein). Example one of GB 2 103 087 describes a two-layered tablet comprising 325 mg paracetamol in one layer, and 200 mg calcium carbonate and 100 mg magnesium carbonate in the other layer. The tablet is prepared by forming a first layer involving dry blending the paracetamol with selected excipients, and forming a second layer by blending the calcium carbonate and magnesium carbonate with corn starch and granulating with starch paste; charging the first layer into a tablet punch, feeding in the second layer and then compressing the combined layers to form a two layered tablet.

According to Shijue et al (Shijue, L. et al, Yiyao Gongye (2); P21-25 (1984)), the addition of calcium carbonate to the formulation of paracetamol tablets may increase dissolution of the tablets; the effervescent effect of calcium carbonate being reported as the major mechanism for improving the dissolution. However the composition details of the tablets are not disclosed, and calcium carbonate is disclosed as being added "externally" to the formulations.

According to Xiuzhi et al (Xiuzhi et al, Chinese Journal of Pharmaceuticals, 1992, 23 (9) 400-402) the addition of calcium carbonate, low substituted hydroxypropyl cellulose or carboxymethyl starch, to paracetamol tablets may accelerate their disintegration or dissolution and increase bioavailability. However neither the composition details of the tablets nor the location of the calcium carbonate in the tablets are disclosed.

WO 98/38983 (SmithKline Beecham) reports that a tablet or capsule formulation containing a combination of sodium bicarbonate and paracetamol, wherein the paracetamol is present in an amount of at least 300 mg and the weight ratio of bicarbonate to paracetamol is at least 0.74 to 1, gives a statistically significant improvement in the rate of absorption over that obtained from a commercially available paracetamol tablet containing no sodium bicarbonate. No improvement was observed when calcium carbonate was combined with paracetamol in a solid dosage form at equivalent levels.

WO 98/38983 (SmithKline Beecham) describes in Comparative Example A, a pharmaceutical composition in the form of a tablet. The tablet, comprising 500 mg paracetamol and 375 mg calcium carbonate (as the antacid component), was formulated as a granule and then compressed into a tablet. In a biostudy reported therein, conducted in fasted volunteers, the $AUC_{0-20}$ was determined to be 76.0 mg·min/L for the tablet, compared to 245 mg·min/L for and 177 mg·min/L for tablets containing sodium bicarbonate as the antacid component. Such a tablet is not a "fast release" tablet, with only 28% of the paracetamol content of the tablet having dissolved at 180 seconds, as determined by the dissolution testing method described herein.

According to Grattan et al, (Grattan T. et al, Eur J Pharm Biopharm. 43(3): 225-229, 2000) paracetamol compositions comprising an antacid component wherein the antacid is 400 mg or 630 mg sodium bicarbonate, show an increased rate of absorption of paracetamol relative to conventional paracetamol tablets containing no antacid in fasted healthy volunteers. The authors suggest that the effect of sodium bicarbonate on paracetamol absorption may be dose dependent.

WO 02/100391 (SmithKline Beecham) discloses a swallow tablet or capsule formulation comprising paracetamol and low levels of an antacid, consisting of sodium or potassium bicarbonate, or mixtures thereof. In a study reported therein where paracetamol tablets containing other antacids were investigated, including various carbonates such as calcium carbonate and sodium carbonate, no significant improvement in the dissolution rate was observed, relative to the rate observed in commercially available paracetamol tablets containing no antacid. Example 6C therein discloses a pharmaceutical composition comprising 500 mg paracetamol and 50 mg calcium carbonate, formulated as a blend comprising a granule admixed with additional ingredients, and compressed into a tablet. The paracetamol was present as an intragranular component of the granule whilst calcium carbonate was present as an extragranular component in the formulation. A further example therein, Example 9, reported that the percentage of paracetamol dissolved from the tablet of Example 6C, at 15 minutes was 40%, compared to 98.5% dissolved (in 15 minutes) from a tablet containing an equivalent amount of sodium bicarbonate (Example 8). It is stated in WO 02/100391 (page 4, lines 8-9) that an enhanced dissolution rate is known in the art to be predictive of an improved absorption rate in vivo. The results of Example 9 indicate that a tablet containing calcium carbonate as an antacid component is likely to confer an inferior pharmacokinetic profile relative to a corresponding tablet containing sodium bicarbonate.

WO2005/115344 (Imaginot Pty) relates to swallow formulations comprising paracetamol which facilitate rapid delivery of paracetamol into the circulatory system.

A swallow formulation is described as comprising paracetamol, one or more pH modulating agents, and one or more agents which facilitate water uptake. Calcium carbonate is one of many listed pH modulating agents, but is not exemplified.

WO2006/049978 (Novartis), filed before but published after the priority date of the present application, relates to compositions comprising paracetamol, caffeine and optionally aspirin, together with an alkaline agent for enhanced absorption e.g. a carbonate, a bicarbonate or mixtures thereof.

It has now been found surprisingly that when tablets are formed from a granulate in which paracetamol and calcium carbonate are combined intragranularly in the presence of a binding agent and a disintegrating agent according to the invention, the dissolution rate is significantly enhanced over conventional paracetamol tablets containing no calcium carbonate, which enhancement is not adversely affected on storage. In comparison when calcium carbonate is present extragranularly (and not intragranularly), the dissolution rate of paracetamol decreases significantly on storage, resulting in variable and unacceptable pharmacokinetics in vivo in a human. A dosage form giving rise to such variable pharmacokinetics would be unlikely to meet with regulatory approval and so would not be viable for commercialization.

Whilst not being bound by any particular theory, calcium carbonate, when used intragranularly in intimate admixture with paracetamol, appears to contribute to the disintegration process, resulting in the formation of fine paracetamol-containing particles that serve to enhance surface area for dissolution. This contribution may be due to alteration of the hydrodynamics of gastric fluid at the fluid/composition interface, aided in part by the effervescence produced by the reaction of carbonate ions with hydrochloric acid. In addition, intragranular calcium carbonate appears to facilitate the formation of a homogenous paracetamol suspension in vivo, which is also believed to enhance dissolution of paracetamol. It is envisaged that a composition according to the invention comprises calcium carbonate as the sole carbonate component, although other carbonates such as magnesium carbonate, sodium bicarbonate or potassium bicarbonate, are not excluded provided they do not adversely impact on the release rate of paracetamol. Accordingly in one embodiment a composition may comprise another carbonate(s) in an amount up to about 5.0% by weight of the composition.

A wide range of particle size and grades of calcium carbonate are commercially available, including directly compressible calcium carbonate, non-compressible calcium carbonate and precipitated calcium carbonate, all of which are suitable for use herein.

In one aspect a pharmaceutical composition according to the invention comprises a low amount of calcium carbonate relative to the paracetamol content. In order to achieve the benefits of small tablet size, high paracetamol content and fast dissolution rate, the ratio of paracetamol to calcium carbonate in the granulate is suitably at least from about 3.0:1.0 for example in one embodiment in the range from about 3.0:1.0 to about 30.0:1.0 such as from about 3.0:1.0 to about 25.0:1.0; in an alternative embodiment from about 5.0:1.0 for example from about 5.0:1.0 to about 30.0:1.0, or from about 5.0:1.0 to about 25.0:1.0, or from about 5.0:1.0 to about 15.0:1.0; in another embodiment from about 8.0:1.0 to about 10.0:1.0; in a further embodiment from about 6.0:1.0 to about 10.0:1.0.

In an alternative aspect a higher amount of calcium carbonate may be used e.g. wherein the weight ratio of paracetamol to calcium carbonate is at least about 1.3:1.0; or in an alternative embodiment, at least 1.5:1.0, without adversely affecting the dissolution rate.

A pharmaceutical composition according to the invention comprises intragranular calcium carbonate. Suitably the calcium carbonate content in the granulate does not exceed 20.0% by weight of the composition, and for example in one embodiment is present in an amount of about 5.0% to about 20.0% by weight, suitably from about 5.0% to about 15.0% by weight of the composition. In an alternative embodiment the calcium carbonate content is from about 8.0% to about 15.0% by weight of the composition.

In one embodiment according to the invention the paracetamol content in the granulate is in the range 70.0 to 80.0% by weight of the composition and the calcium carbonate in the granulate is in the range 8.0% to 15.0% by weight of the composition. For example a 500 mg paracetamol composition may comprise 30 mg to 110 mg intragranular calcium carbonate, and a 325 mg paracetamol composition may comprise intragranular 20 mg to 72 mg calcium carbonate.

Whilst calcium carbonate is present as an intragranular component, it is recognized that a limited amount of calcium carbonate e.g. up to about an additional 25.0% by weight of the intragranular calcium carbonate content of the composition, may also be present extragranularly. In one embodiment a composition according to the invention comprises, as an extragranular component, calcium carbonate in an amount ranging from about 0.1% to about 10.0% by weight of the intragranular calcium carbonate amount therein.

A composition according to the invention comprises intragranularly, a component that functions as a binder, such as one or more binding agents. Suitably the binding agent may comprise a first binding agent and a second binding agent. Suitable binding agents for use herein include conventional binding agents used in the art such as starches, polymers and cellulose derivatives or combinations thereof.

If the binding agent includes a starch, suitably it is of vegetable origin such as corn (or maize) starch, modified corn starch, wheat starch, modified wheat starch, potato starch, or pregelatinized starch e.g. available commercially as Starch 1500 G or Prejel; or a combination of two or more thereof. Combinations of starch with other binding agents, such as those described herein, are also envisaged within the scope of the invention. In one embodiment, suitably the starch is pregelatinzed starch, where it is the sole or a first binding agent. Pregelatinized starch is a starch that has been chemically and/or mechanically processed. Typically pregelatinized starch contains 5% of free amylase, 15% of free amylopectin, and 80% unmodified starch. Pregelatinized starch may be obtained from corn (or maize), potato or rice starch. Paracetamol dissolution rate is adversely affected in a composition comprising, as intragranular components, paracetamol, calcium carbonate, maize starch, pregelatinized starch, Povidone K25, and potassium sorbate, and wherein the weight ratio of pregelatinized starch to maize starch is about 2.3:1. Accordingly if the binding agent comprises a mixture of corn (or maize) starch and pregelatinized starch, then the weight ratio of pregelatinized starch to corn (or maize) starch is at least 3.0:1.0. In one embodiment the weight ratio of pregelatinized starch to corn (or maize) starch is at least 5.0:1.0.

Suitably, when present in a composition of the invention, the starch is present in the granulate in an amount from about 1.0% to about 30.0% by weight of the composition, typically from about 5.0% to about 20.0% for example from about 8.0% to about 15.0% by weight of the composition.

If the binding agent includes a polymer, suitably it is polyvinyl pyrrolidone or povidone (PVP), polyvinyl alcohol (PVA), polyethylene oxide, polaxamer, polymethacrylate e.g. a carbomer, polyethylene glycol (PEG) such as PEG 3350 and calcium polycarbophil; or a combination of two or more thereof. Combinations of a polymer with other binding agents, such as those described herein, are also envisaged within the scope of the invention. When the polymer comprises PVP, it will suitably comprise a molecular weight of about 30,000 e.g. available commercially as PVP K25. Suitably, when present in a composition of the invention, the polymer is present in the granulate in an amount from about 1.0% to about 10.0% by weight of the composition, typically from about 1.5% to about 5.0% by weight of the composition.

In one embodiment, a polymer such as PVP is present as a second binding agent. In one embodiment a starch such as pregelatinized starch is present as a first binding agent, in an amount ranging from about 10.0% to about 15.0% by weight of the composition, and a polymer such as PVP is present as a second binding agent in an amount ranging from about 1.5% to about 5.0% by weight of the composition. Suitably such an embodiment is substantially free of corn (or maize) starch, for example comprising no more than an amount ranging from about 0.0% to about 1.0% of corn (or maize) starch.

If the binding agent includes a cellulosic derivative, suitably it is hydroxypropyl cellulose (HPC) (low to medium viscosity versions thereof) e.g. as may be available commercially under the brand name Klucel® from the Aqualon division of Hercules Inc., Dow Chemical Company e.g. Klucel GF, Klucel JF, Klucel LF and Klucel EF; hydroxypropylmethyl cellulose (HPMC) (low to medium viscosity versions thereof) e.g. as may be available commercially under the brand name Methocel® from the Dow Chemical Company e.g. Methocel E15Premium, Methocel E3Premium LV, Methocel K100LV; microcrystalline cellulose (MCC), carboxymethylcellulose (MC), sodium carboxymethylethyl cellulose; or a combination of two or more thereof. Combinations of a cellulosic derivative with other binding agents noted above are also envisaged within the scope of the invention. The term "low to medium" viscosity as used herein means a viscosity in the range of from about 15 to about 1000 mPa·s. It is recognized in the art that the determination of the viscosity of cellulosic derivatives is based upon standard techniques and grading in the art e.g. for HPMC, viscosity may be determined at 20° C. with a 2% solution using a Ubbelohde viscometer, or for HPC, viscosity may be determined at 25° C. with a 2-10% solution using a Brookfield LVF viscometer. Generally the cellulosic derivative is present in the granulate in an amount ranging from about 0.5% to about 5.0% by weight of the composition. It is recognized in the art that certain cellulosic derivatives, such as HPMC, will have varying roles in a formulation, depending upon the amount used. For example HPMC (low or medium viscosity) may function as a binding agent, a coating agent, or as a matrix forming agent. It has been found that when HPMC (low or medium viscosity) is used at about 10.0% by weight of the composition, the dissolution rate of paracetamol is slowed down, probably owing to the extended-release properties of HPMC. According to the present invention, when used as a binding agent, the HPMC is present in an amount typically not more than 2.5% by weight of the composition, for example in an amount from about 1.0% to about 2.5% by weight of the composition.

The total amount of binding agent present intragranularly in a composition according to the invention is suitably in an amount ranging from about 1.0% to about 30.0% by weight of the composition, for example from about 2.0% to about 25.0% by weight of the composition, or alternatively from about 5.0% to about 20.0% by weight of the composition.

Whilst a binding agent is present as an intragranular component, it is recognized that a modest amount of binding agent e.g. up to about an additional 5.0%-10.0% by weight of the intragranular binding agent content of the composition, may also be present extragranularly. In one embodiment a composition according to the invention comprises, as an extragranular component, a binding agent in an amount ranging from about 0.1% to about 10.0% by weight of the intragranular binding agent amount therein.

A composition according to the invention comprises, as an intragranular component, a component that functions as a disintegrant, such as one or more disintegrating agents. Suitable disintegrating agents include a non-super disintegrant, a super disintegrant or a combination of both. Suitable non-super disintegrants include conventional disintegrants such as starch (corn or maize), pregelatinized starch e.g. Starch 1500 G, clays (Veegum or Bentonite), microcrystalline cellulose, cellulose or powdered cellulose. It is recognized in the art, that some excipients may perform more than one role in a given pharmaceutical formulation. For example certain excipients, e.g. starches including pregelatinized starch, and microcrystalline cellulose (hereinbefore identified as binding agents) function as both binders and disintegrants. Accordingly it will be understood that the same excipient, may act as both binding agent and disintegrating agent. In such cases, inclusion of a disintegrating agent in addition to a binding agent is entirely optional. Equally, in such cases, inclusion of a binding agent in addition to a disintegrating agent is entirely optional.

One aspect of the invention provides a pharmaceutical composition, such as a swallow tablet, comprising as intragranular components, paracetamol; calcium carbonate; at least one binding agent which is microcrystalline cellulose or starch, wherein the starch is corn (or maize) starch, modified corn starch, wheat starch, modified wheat starch, potato starch, pregelatinized starch or a combination of two or more starches thereof, with the proviso that if the binding agent comprises a mixture of corn (or maize) starch and pregelatinized starch then the weight ratio of pregelatinized starch to corn (or maize) starch is greater than from about 3.0 to 1.0; and optionally a disintegrating agent; and one or more pharmaceutically acceptable ingredients as extragranular components.

A non-super disintegrant may be present intragranularly, extragranularly or both intragranularly and extragranularly. When a non-super disintegrant is either absent from the composition or is present only extragranularly, the disintegrating agent will comprise a super disintegrant, present intragranularly. Suitably a non-super disintegrant will be present intragranularly in an amount ranging from about 5.0% to about 30.0% by weight of the composition, suitably from about 5.0% to about 20.0% by weight of the composition. When present extragranularly, the non-super disintegrating agent, may also be present in an amount for example up to about an additional 5.0%-10.0% by weight of the intragranular non-super disintegrating agent content of the composition.

"Super disintegrants" represent a class of disintegrating agent which may generally be used in lower amounts in pharmaceutical preparations, as compared to conventional disintegrants. Examples of super disintegrants include sodium starch glycolate, the sodium salt of carboxymethyl starch, modified cellulose and cross-linked polyvinyl pyrrolidone. Sodium starch glycolate is available commercially under the trade names Explotab® (Edward Mendell Co.), Primojel® (Generichem Corp) and Tablo® (Blanver, Brazil). An example of modified cellulose includes croscarmellose, the sodium salt of carboxymethyl cellulose. Croscarmellose is available commercially under the trade names AcDiSol® (FMC Corp.), Nymcel ZSX® (Nyma, Netherlands), Primellose® (Avebe, Netherlands), Solutab® (Blanver, Brazil). An example of a cross-linked polyvinyl pyrrolidone includes crospovidone, and is commercially available under the trade names Kollidon CL® or Kollidon CL-M (Basf Corp.), and Polyplasdone XL® (ISP Corp). Suitably the disintegrating agent comprises cross-linked polyvinyl pyrrolidone. When present, a super disintegrant may be present intragranularly, extragranularly or both intragranularly and extragranularly. It is recognized that when a super disintegrant is either absent from the composition or is present only extragranularly, the disintegrating agent will comprise a non-super disintegrant, present intragranularly. A super disintegrant may be used intragranularly or extragranularly, in an amount ranging from about 0.5% to about 5.0% by weight of the composition. The total amount of super disintegrant may be in an amount ranging from about 0.5% to about 10.0% by weight of the composition.

A composition according to the invention may optionally contain further additional pharmaceutically acceptable extragranular components. For example a composition according to the invention may comprise a hydrophilic colloid such as alginic acid, carrageenan, gellan, pectin and/or agar, as an extragranular component. Suitably the hydrophilic colloid is alginic acid. When present, a hydrophilic colloid is present in an amount ranging from about 1.0% to about 5.0% by weight of the composition.

In one aspect a composition according to the invention comprises alginic acid as an extragranular component. Whilst not being bound by any particular theory, it is believed that calcium alginate, formed by the reaction of calcium ions with alginic acid in the acidic environs of the stomach, in combination with carbon dioxide, generated from the calcium carbonate, facilitates the formation of a uniform suspension of fine particles with increased surface area leading to enhanced dissolution.

Other pharmaceutically acceptable extragranular components include, but are not limited to, an antimicrobial agent e.g. potassium sorbate or a paraben i.e. one or more hydroxy benzoic acid esters e.g. methyl, ethyl, propyl or butyl, suitably singularly or as mixtures. Advantageously use of a paraben, such as may be available commercially under the Nipa® brand name, e.g. Nipasept® sodium, enables an efficient production process with less frequent need for equipment clean down between production runs.

Additional pharmaceutically acceptable extragranular components include a dye; colorant; flavorant; compression aid; preservative; wetting agent; bulking agent; adhesive; sweetening agent; lubricant such as magnesium stearate, calcium stearate, sodium stearate, stearic acid or talc; and a flow aid or glidant such as colloidal silicon dioxide (Cab-O-Sil, Syloid™). Suitably, when present, a lubricant or flow aid are each used in an amount ranging from 0.1% to 5.0% by weight of the composition. It is recognized that additional pharmaceutically acceptable components may be present as intragranular components as well as extragranular components.

When the composition is in a tablet form, it may further comprise a film coat e.g. HPMC. Suitably the film coat is a transparent film coat e.g. a dye, although an opaque film coat e.g. as obtained when using a film coat in combination with an opacifier or a pigment such as titanium dioxide or a lake may also be used. For example one commercially available film coat is an Opadry coating system from Colorcon.

In addition to paracetamol, compositions of the invention may also contain other pharmaceutically active agents for example other analgesics such as codeine, hydrocodone, oxycodone, tramadol and propoxyphene; anti-inflammatory analgesics such as NSAIDs e.g. aspirin and ibuprofen; decongestants such as pseudoephedrine and phenylephrine; antitussives such as pholcodine and dextromethorphan; expectorants such as guaifenesin and bromhexine; diuretics such as pamabrom; non-sedating and sedating antihistamines such as diphenydramine, doxylamine and mepyramine; gastrointestinal agents such as metoclopramide; triptans such as sumatriptan; and muscle relaxants such as methocarbamol. Compositions may also contain a pharmaceutically acceptable adjuvant, for example caffeine. Pharmaceutically active agents and adjuvants e.g. may be present intragranularly, extragranularly or both intragranularly and extragranularly.

In one aspect according to the invention there is provided a composition comprising pseudoephedrine intragranularly, extragranularly or both intragranularly and extragranularly. Suitably the pseudoephedrine is present intragranularly. In another aspect there is provided a composition comprising caffeine intragranularly, extragranularly or both intragranularly and extragranularly. Suitably the caffeine is present extragranularly.

The term "pharmaceutically active agent" includes, but is not limited to, drugs, nutritional agents, as described herein. This term includes bioactive agents, active agents, therapeutic agents, or drug(s) as defined herein, and follows the guidelines from the European Union Guide to Good Manufacturing Practice. Such substances are intended to furnish pharmacological activity or other direct effect in the cure, mitigation, treatment, or prevention of disease or to affect the structure and function of the body. The pharmacological activity may be prophylactic, or for treatment of a disease state.

Drug substances include those intended for oral administration. A description of these classes of drugs and a listing of species within each class can be found in Martindale, The Extra Pharmacopoeia, Twenty-ninth Edition, The Pharmaceutical Press, London, 1989. The drug substances are commercially available and/or can be prepared by techniques known in the art.

The following Examples (1 to 6) are illustrations of the invention. Examples 7 and 8 include examples falling both inside and outside the scope of the invention. Examples 9 and 10 are comparative examples, falling outside the scope of the invention but are included herein to further demonstrate the advantages of the invention.

EXAMPLES

Example 1

Granules for compression into tablets were prepared from the following ingredients (1-6):

| Ingredients | Percentage |
| --- | --- |
| 1. Paracetamol (fine) | 76.78 |
| 2. Starch, pregelatinized | 11.52 |
| 3. Calcium carbonate | 10.14 |
| 4. Povidone (K-25) | 0.38 |
| 5. Crospovidone | 0.91 |
| 6. Potassium sorbate | 0.09 |
| 7. granulation from above | 99.82 |
| 8. Colloidal silicon dioxide | 0.06 |
| 9. Magnesium stearate | 0.12 |
| Total | 100.00 |

Ingredients 1-6 sieved were through a 20 mesh sieve into a suitable mixer and granulated with a suitable quantity of deionized water to form medium to heavy granules. The granules were dried in a suitable oven at 40-50° C., until the moisture (water content) was less than 2%. The resulting dried granules were then passed through a 12 mesh sieve to give white granules. The granules thus produced (7) were mixed in a suitable blender with ingredients 8-9. The resulting blend was then compressed into tablets using suitable capsule shaped tooling to give capsule shaped tablets.

Example 2

Granules for compression into tablets were prepared from the following ingredients (1-6), as per Example 1:

| Ingredients | Percentage |
| --- | --- |
| 1. Paracetamol (fine) | 75.05 |
| 2. Starch, pregelatinized | 11.26 |
| 3. Calcium carbonate | 9.91 |
| 4. Povidone (K-25) | 0.38 |
| 5. Crospovidone | 0.88 |
| 6. Potassium sorbate | 0.09 |
| 7. granulation from above | 97.57 |
| 8. Alginic acid | 2.25 |
| 9. Colloidal silicon dioxide | 0.06 |
| 10. Magnesium stearate | 0.12 |
| Total | 100.00 |

The granules thus produced (7) were mixed in a suitable blender with ingredients 8-10. The resulting blend was then compressed into tablets using suitable capsule shaped tooling to give capsule shaped tablets.

Example 3

Granules for compression into tablets were prepared from the following ingredients (1-6), as per Example 1:

| Ingredients | Percentage |
| --- | --- |
| 1. Paracetamol (fine) | 75.05 |
| 2. Starch, pregelatinized | 11.26 |
| 3. Calcium carbonate | 9.91 |
| 4. Povidone (K-25) | 0.38 |
| 5. Crospovidone | 0.88 |
| 6. Potassium sorbate | 0.09 |
| 7. granulation from above | 97.57 |
| 8. Agar | 2.25 |
| 9. Colloidal silicon dioxide | 0.06 |
| 10. Magnesium stearate | 0.12 |
| Total | 100.00 |

The granules thus produced (7) were mixed in a suitable blender with ingredients 8-10. The resulting blend was then compressed into tablets using suitable capsule shaped tooling to give capsule shaped tablets.

Example 4

Compositions for compression into tablets (Examples A-F) were prepared from the ingredients below, using the methodology of Example 1. Some of the tablets prepared were subsequently coated using HPMC as the film coat containing an opacifier (titanium dioxide). The tablets were warmed in a coating pan of suitable size. Once the tablet bed reached a temperature of 40-45° C., the coating solution was applied and then the tablets were cured by allowing the bed cool to about 30-35° C. Following this, the tablets were waxed and unloaded to suitable containers.

Examples D and F, correspond respectively to the formulations of Examples 2 and 1 herein respectively.

| Ingredients | Example A % (w/w) | Example B % (w/w) | Example C % (w/w) | Example D % (w/w) | Example E % (w/w) | Example F % (w/w) |
| --- | --- | --- | --- | --- | --- | --- |
| 1. Paracetamol (fine) | 71.20 | 73.89 | 72.76 | 75.05 | 75.80 | 76.78 |
| 2. Starch, pregelatinized | 10.68 | 11.08 | 10.91 | 11.26 | 11.37 | 11.52 |
| 3. Calcium carbonate | 9.40 | 9.75 | 9.60 | 9.91 | 10.00 | 10.14 |
| 4. Povidone (K-25) | 0.36 | 0.37 | 0.36 | 0.38 | 0.38 | 0.38 |
| 5. Crospovidone | 0.84 | 0.87 | 0.86 | 0.88 | — | 0.91 |
| 6. Potassium sorbate | 0.09 | 0.09 | 0.09 | 0.09 | 0.09 | 0.09 |
| 7. granulation from above | 92.57 | 96.05 | 94.58 | 97.57 | 97.64 | 99.82 |
| 8. Alginic acid | 2.14 | 2.22 | 2.18 | 2.25 | 2.27 | — |
| 9. Crospovidone | 2.99 | 1.55 | 3.06 | — | — | — |
| 10. Citric acid | 2.14 | — | — | — | — | — |
| 11. Colloidal silicon dioxide | 0.05 | 0.06 | 0.06 | 0.06 | — | 0.06 |
| 12. Magnesium stearate | 0.11 | 0.12 | 0.12 | 0.12 | 0.09 | 0.12 |
| Total | 100.00 | 100.00 | 100.00 | 100.00 | 100.00 | 100.00 |

Dissolution Studies

Dissolution studies were conducted on tablets from Examples A to F using the USP paddle apparatus rotating at 30 rpm with 900 mL of 0.05 M HCl at 37° C. as dissolution medium. The amount of paracetamol dissolved after 180 seconds (for both coated and uncoated tablets) is shown in Table 1:

TABLE 1

| Example | % APAP released in uncoated/coated tablets (Initial) | % APAP released in uncoated/coated tablets (at 10 days)* |
|---|---|---|
| A | 94/88 | 85/80 |
| B | 97/78 | 79/76 |
| C | 91/94 | 91/85 |
| D | 94/86 | 89/79 |
| E | 90/not tested | 75/not tested |
| F | 75/not tested | 65/not tested |

- following exposure in Petri dish @ 40° C./75% RH

Results

The results show that Examples A-F exhibit commercially acceptable dissolution rates, including following storage under stressed conditions.

Example 5

Compositions according to Examples G to I, were prepared for compression into tablets, using the methodology of Example 1.

| Ingredients | Example G (% w/w) | Example H (% w/w) | Example I (% w/w) |
|---|---|---|---|
| 1. Paracetamol (fine) | 75.80 | 75.80 | 75.12 |
| 2. Starch, pregelatinized | 11.37 | 11.37 | — |
| 3. Calcium carbonate | 10.00 | 10.00 | 9.92 |
| 4. Povidone (K-25) | — | — | 0.37 |
| 5. HPMC | 0.38 | — | — |
| 6. Microcrystalline cellulose | — | 0.38 | 11.27 |
| 7. Crospovidone | — | — | 0.89 |
| 8. Potassium sorbate | 0.09 | 0.09 | 0.09 |
| 9. granulation from above | 97.64 | 97.64 | 97.66 |
| 10. Alginic acid | 2.27 | 2.27 | 2.25 |
| 11. Magnesium stearate | 0.09 | 0.09 | 0.09 |
| Total | 100.00 | 100.00 | 100.00 |

Dissolution Studies

Dissolution studies were conducted on coated and uncoated tablets from Examples G to I using the USP paddle apparatus II rotating at 30 rpm with 900 mL of 0.05 M HCl at 37° C. as dissolution medium. The amount of paracetamol dissolved after 180 seconds is shown in Table 2:

TABLE 2

| Example | % APAP released in uncoated tablets (Initial) | % APAP released in uncoated tablets (at 10 days)* |
|---|---|---|
| G | 74 | 72 |
| H | 69 | 61 |
| I | 80 | 77 |

*following exposure in Petri dish @ 40° C./75% RH

Results

The results show that Examples G, H, and I exhibit commercially acceptable dissolution rates, including following storage under stressed conditions.

Example 6

Tablets within the scope of the invention were prepared with the following composition:

| Ingredients | % |
|---|---|
| 1. Paracetamol (fine), Ph. Eur. | 74.83 |
| 2. Pregelatinized Starch, Ph. Eur. | 11.22 |
| 3. Povidone (K-25), Ph. Eur. | 0.37 |
| 4. Preservative, Ph. Eur. | 0.09 |
| 5. Crospovidone, Ph. Eur. | 0.88 |
| 6. Calcium carbonate, Ph. Eur. | 9.88 |
| 7. Alginic acid, Ph. Eur. | 2.24 |
| 8. Glidant Ph. Eur. | 0.06 |
| 9. Lubricant, Ph. Eur. | 0.12 |
| 10. Film coat | 0.30 |
| 11. Polishing wax. | 0.01 |
| Total | 100.00 |

Items 1-6 were screened, mixed and then granulated with deionised water in a suitable granulator. The resulting granules was then dried using a fluid bed drier and then screened and blended with items 7, 8 and 9 before being compressed into capsule shaped tablets (target paracetamol content 500 mg) using a suitable tablet press. The resulting white tablets were then spray coated with a mixture of item 10 and deionised water, using a suitable spray coating drum. Item 11 was then applied to provide a suitable polish to the tablets.

Example 7

Samples of commercially available Paracetamol 500 mg tablets were sourced from a number of European markets and then tested together with Example 6 using the dissolution method outlined in Example 4. 12 tablets of each product were tested in each case. The mean release rate profiles are shown below in Table 3. The mean % released at 3 minutes, the range and the coefficient of variation (CV) at 3 minutes are shown in the table below. For example 7, dissolution was rapid and essentially complete after 3 minutes with a very low variability between tablets as demonstrated by the low value (1.5%) for the CV for the 3 minute dissolution value. In contrast, all of the other paracetamol tablets dissoluted slowly and with a high degree of variability between tablets as illustrated by a high CV (>10%) for the 3 minute dissolution values in all cases.

TABLE 3

| Product | Mean % released at 3 minutes | Minimum (%) | Maximum (%) | CV |
|---|---|---|---|---|
| Example 6 | 87.9 | 85.8 | 89.7 | 1.59 |
| Commercial product A | 16.3 | 6.6 | 21.5 | 27.3 |
| Commercial product B | 19.9 | 14.6 | 27.0 | 23.66 |
| Commercial product C | 16.3 | 11.0 | 22.2 | 24.94 |
| Commercial product D | 15.1 | 7.0 | 22.7 | 36.90 |
| Commercial product E | 16.5 | 11.6 | 22.6 | 22.79 |
| Commercial product F | 15.1 | 10.1 | 24.4 | 27.66 |
| Commercial product G | 14.9 | 11.0 | 18.4 | 18.24 |
| Commercial product H | 12.6 | 7.3 | 16.5 | 23.00 |
| Commercial product I | 13.6 | 10.9 | 16.6 | 12.12 |
| Commercial product J | 32.1 | 22.3 | 36.5 | 12.96 |
| Commercial product K | 30.1 | 20.4 | 43.0 | 27.95 |

Example 8

The following products were compared in a two way crossover, pharmacokinetic study employing 75 healthy, fed volunteers.
Treatment A: Commercial product A from Example 7
Treatment B: Paracetamol tablets from Example 6

Each volunteer swallowed 2 tablets of one of the formulations with 150 mls of water on two separate occasions at least one day apart. Blood samples were taken at regular intervals post dose and plasma paracetamol levels were determined by HPLC. Pharmacokinetic profiles (paracetamol plasma concentration vs. time) were produced for each volunteer on each treatment and individual area under the plasma concentration time curves between 0 and 30 minutes ($AUC_{0-30}$) were derived. The $AUC_{0-30}$ values for each treatment were then compared, see Table 4 below. The median value for $AUC_{0-30}$ was significantly greater (p<0.00001) for treatment B (0.98 µg.h/ml) compared to treatment A (0.10 µg.h/ml). In addition, the between subject variability in $AUC_{0-30}$ was significantly less (p<0.0001) for treatment B (CV 84.42%) compared to treatment A (192.03%).

TABLE 4

|  | Median AUC 0-30 (µg · h/ml) | CV (%) |
|---|---|---|
| Treatment A: Commercial product A from Example 7 | 0.10 | 192.03 |
| Treatment B: Paracetamol tablets from Example 6 | 0.98 | 84.42 |

Additional Comparative Examples Falling Outside the Scope of the Invention

Example 9

Comparative Examples J-L

Comparative Examples J to L below, containing extragranular calcium carbonate were prepared and are included herein for comparative purposes only.

Compositions for compression into tablets were prepared, using the methodology of Example 1. Some of the tablets prepared were subsequently coated using HPMC as the film coat containing an opacifier (titanium dioxide). The tablets were warmed in a coating pan of suitable size. Once the tablet bed reached a temperature of 40-45° C., the coating solution was applied, and then the tablets were cured by allowing the bed cool to about 30-35° C. Following this, the tablets were waxed and unloaded to suitable containers.

| Ingredients | Example J (% w/w) | Example K (% w/w) | Example L (% w/w) |
|---|---|---|---|
| 1. Paracetamol (fine) | 71.20 | 72.76 | 75.80 |
| 2. Starch, pregelatinized | 10.68 | 10.91 | 11.37 |
| 3. Povidone (K-25) | 0.36 | 0.36 | 0.38 |
| 4. Crospovidone | 0.84 | 0.86 | — |
| 5. Potassium sorbate | 0.09 | 0.09 | 0.09 |
| 6. granulation from above | 83.17 | 84.98 | 87.63 |
| 7. Calcium carbonate | 9.40 | 9.60 | 10.00 |
| 8. Alginic acid | 2.14 | 2.18 | 2.27 |
| 9. Crospovidone | 2.99 | 3.06 | — |
| 10. Citric acid | 2.14 | — | — |
| 11. Colloidal silicon dioxide | 0.05 | 0.06 | — |
| 12. Magnesium stearate | 0.11 | 0.12 | 0.09 |
| Total | 100.00 | 100.00 | 100.00 |

Dissolution Studies

Dissolution studies were conducted on coated and uncoated tablets from Examples J, K and L using the USP paddle apparatus II rotating at 30 rpm with 900 mL of 0.05 M HCl at 37° C. as dissolution medium. The amount of paracetamol dissolved after 180 seconds (for both coated and uncoated tablets) is shown in Table 5:

TABLE 5

| Example | % APAP released in uncoated/coated tablets (Initial) | % APAP released in uncoated/coated tablets (at 5 days)* |
|---|---|---|
| J | 87/85 | 68/48 |
| K | 80/69 | 64/27 |
| L | 83/66 | 60/1.5 |

*following exposure in Petri dish @ 40° C./75% RH

Results

The results show that Examples J-L exhibit commercially unacceptable dissolution characteristics following storage under stressed conditions after a relatively short period (5 days).

Example 10

Dissolution studies were conducted on tablets disclosed in the prior art (Example 10M and 10N), and on a further tablet, containing extragranular calcium carbonate. The dissolution method employed used a USP paddle apparatus rotating at 30 rpm with 900 mL of 0.05 M HCl at 37° C. as dissolution medium. The amount of paracetamol dissolved after 180 seconds is shown in Table 6:

TABLE 6

| Example | | % APAP released at 180 seconds | % APAP released (at 10 days)* |
|---|---|---|---|
| 10M. | Tablet from WO98/38983 (Comparative Example A) | 28 | Not determined |
| 10N. | Tablet from WO02/100391 (Example 6C) | 2 | Not determined |
| 10P. | Tablet comprising extra-granular calcium carbonate | 84 | 29 |

*following exposure in Petri dish @ 40° C./75% RH

Example 10P

Granules for compression into tablets were prepared from the following ingredients (1-5) as per Example 1:

| Ingredients | 10P % (w/w) |
|---|---|
| 1. Paracetamol (fine) | 75.05 |
| 2. Starch, pregelatinized | 11.26 |
| 3. Povidone (K-25) | 0.37 |
| 4. Crospovidone | 0.89 |
| 5. Potassium sorbate | 0.09 |
| granulation from above | 87.66 |
| 6. Calcium carbonate | 9.91 |
| 7. Alginic acid | 2.25 |
| 8. Colloidal silicon dioxide | 0.06 |
| 9. Magnesium stearate | 0.12 |
| Total | 100.00 |

The granules thus produced were mixed in a suitable blender with ingredients 6-9 and the resulting blend then compressed into tablets.

Results

Formulation examples 10M and 10N provided tablets exhibiting significantly lower dissolution rates compared to those of the present invention. The initial dissolution rate observed for a tablet according to 10P was fast, however, this was not maintained following storage under stressed conditions.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

The invention claimed is:

1. A pharmaceutical composition comprising paracetamol, calcium carbonate in a ratio of paracetamol to calcium carbonate of 3.0: 1.0 to 30.0: 1.0, at least one binding agent, and at least one disintegrating agent, as intragranular components in the form of a granulate, and wherein at least 60% of the paracetamol is released from the composition at 180 seconds as determined by a dissolution method that utilizes a USP paddle apparatus rotating at 30 rpm, employing 900 ml of 0.05M HCl, following storage of the composition for ten days in an open Petri dish at 40° C.±2° C., and 75% RH±5% RH.

2. A pharmaceutical composition according to claim 1 wherein the intragranular binding agent comprises a starch, a polymer, a cellulose derivative or a combination of two or more thereof.

3. A pharmaceutical composition according to claim 2 wherein the intragranular binding agent comprises a cellulose derivative which is microcrystalline cellulose.

4. A pharmaceutical composition according to claim 2 wherein the intragranular binding agent comprises a starch wherein the starch is corn (or maize) starch, modified corn starch, wheat starch, modified wheat starch, potato starch or pregelatinized starch, or a combination of two or more thereof with the proviso that if the binding agent comprises a mixture of corn (or maize) starch and pregelatinized starch then the weight ratio of pregelatinized starch to corn starch is greater than from about 3.0 to 1.0.

5. A pharmaceutical composition according to claim 1 wherein the intragranular binding agent comprises pregelatinized starch.

6. A pharmaceutical composition according to claim 2 wherein the starch is present in an amount ranging from about 5.0% to about 20.0% by weight of the composition.

7. A pharmaceutical composition according to claim 2 wherein the intragranular binding agent comprises a polymer selected from povidone (PVP), polyvinyl alcohol (PVA), polyethylene oxide, polaxamer, polymethacrylate, a carbomer, polyethylene glycol (PEG) and calcium polycarbophil, or a combination of two or more thereof, present in an amount ranging from about 1.5% to about 5.0% by weight of the composition.

8. A pharmaceutical composition according to claim 2 wherein the intragranular binding agent comprises a cellulose derivative selected from hydroxypropyl cellulose (HPC), hydroxypropylmethyl cellulose (HPMC), microcrystalline cellulose (MCC), carboxymethylcellulose (MC), and sodium carboxymethylethyl cellulose; or a combination of two or more thereof.

9. A pharmaceutical composition according to claim 1 wherein the intragranular binding agent comprises a first binding agent and a second binding agent.

10. A pharmaceutical composition according to claim 9 wherein the first binding agent is pregelatinized starch in an amount ranging from about 5.0% to about 20.0% by weight of the composition and the second binding agent is PVP in an amount ranging from about 1.5% to about 15.0% by weight of the composition.

11. A pharmaceutical composition according to claim 1 wherein the intragranular disintegrating agent comprises a super disintegrant selected from sodium starch glycolate, the sodium salt of carboxymethyl starch, cross-linked polyvinyl pyrrolidone, croscarmellose and the sodium salt of carboxymethyl cellulose.

12. A pharmaceutical composition according to claim 11 wherein the super disintegrant is cross-linked polyvinyl pyrrolidone.

13. A pharmaceutical composition according to claim 11 wherein the super disintegrant is in an amount ranging from about 0.5 to about 5.0% by weight of the composition.

14. A pharmaceutical composition according to claim 1 wherein the intragranular binding agent and the intragranular disintegrating agent are the same excipient.

15. A pharmaceutical composition according to claim 14 wherein the said same excipient is pregelatinized starch.

16. A pharmaceutical composition according to claim 15 wherein the pregelatinized starch is present in an amount ranging from about 5.0 to about 20.0% by weight of the composition.

17. A pharmaceutical composition according to claim 1 wherein the intragranular paracetamol is present in an amount ranging from about 60.0% to about 80.0% by weight of the composition.

18. A pharmaceutical composition according to claim 1 wherein the intragranular calcium carbonate is present in an amount ranging from about 5.0% to about 20.0% by weight of the composition.

19. A pharmaceutical composition according to claim 1 comprising at least one extragranular component.

20. A pharmaceutical composition according to claim 19 wherein the extragranular component comprises a binding agent in an amount ranging from about 0.1% to about 10.0% by weight of the intragranular binding agent.

21. A pharmaceutical composition according to claim 19 wherein the extragranular component comprises calcium carbonate in an amount ranging from about 0.1% to about 10.0% by weight of the intragranular calcium carbonate.

22. A pharmaceutical composition according to claim 19 wherein the extragranular component comprises paracetamol in an amount ranging from about 0.1% to about 10.0% by weight of the intragranular paracetamol.

23. A pharmaceutical composition according to claim 19 wherein the extragranular component comprises a super disintegrant in an amount ranging from about 0.1% to about 5.0% by weight of the composition.

24. A pharmaceutical composition according to claim 19 wherein the extragranular component comprises a hydrophilic colloid.

25. A pharmaceutical composition according to claim 24 wherein the hydrophilic colloid is selected from alginic acid, carrageenan, gellan, pectin, agar or a combination of two or more thereof.

26. A pharmaceutical composition according to claim 25 wherein the hydrophilic colloid comprises alginic acid.

27. A pharmaceutical composition according to claim 24 wherein the hydrophilic colloid is present in an amount ranging from about 1.0% to about 5.0% by weight of the composition.

28. A pharmaceutical composition according to claim 19 wherein the extragranular component comprises at least one pharmaceutically active agent, pharmaceutically acceptable adjuvant selected from caffeine, colorant, dye, flavorant, sweetener, lubricant, glidant, or a combination of two or more thereof.

29. A pharmaceutical composition according to claim 28 in a unit dosage form.

30. A pharmaceutical composition according to claim 29 in the form of a swallow tablet.

31. A pharmaceutical composition according to claim 7 wherein the intragranular binding agent is PEG 3350.

\* \* \* \* \*